(12) United States Patent
Murphy et al.

(10) Patent No.: US 8,078,262 B2
(45) Date of Patent: Dec. 13, 2011

(54) METHOD FOR IMAGING AND SPECTROSCOPY OF TUMORS AND DETERMINATION OF THE EFFICACY OF ANTI-TUMOR DRUG THERAPIES

(75) Inventors: John C Murphy, Clarksville, MD (US); Jerry R. Williams, Arlington, TX (US); Robert Osiander, Ellicott City, MD (US)

(73) Assignee: The Johns Hopkins University, Baltimore, MD (US)

(*) Notice: Subject to any disclaimer, the term of this patent is extended or adjusted under 35 U.S.C. 154(b) by 2037 days.

(21) Appl. No.: 10/474,977

(22) PCT Filed: Apr. 15, 2002

(86) PCT No.: PCT/US02/11718
§ 371 (c)(1),
(2), (4) Date: Jun. 14, 2002

(87) PCT Pub. No.: WO02/082988
PCT Pub. Date: Oct. 24, 2002

(65) Prior Publication Data
US 2004/0236225 A1    Nov. 25, 2004

(51) Int. Cl.
*A61B 6/00* (2006.01)
(52) U.S. Cl. .................... 600/473; 600/475; 600/478
(58) Field of Classification Search .......... 600/309–344, 600/407, 408, 473–480, 549; 607/1, 88–95, 607/356, 359, 250; 606/1–19
See application file for complete search history.

(56) References Cited

U.S. PATENT DOCUMENTS

| | | | | |
|---|---|---|---|---|
| 5,003,979 | A | * | 4/1991 | Merickel et al. ............ 600/410 |
| 5,810,010 | A | * | 9/1998 | Anbar ............................ 600/474 |
| 5,814,040 | A | * | 9/1998 | Nelson et al. .................... 606/9 |
| 5,951,546 | A | * | 9/1999 | Lorentzen ....................... 606/41 |
| 5,983,124 | A | * | 11/1999 | Carr ............................... 600/407 |
| 5,999,840 | A | * | 12/1999 | Grimson et al. .............. 600/424 |
| 6,023,637 | A | * | 2/2000 | Liu et al. ....................... 600/474 |
| 6,081,612 | A | * | 6/2000 | Gutkowicz-Krusin et al. ............................ 382/128 |
| 6,478,793 | B1 | * | 11/2002 | Cosman et al. ................ 606/34 |
| 6,602,274 | B1 | * | 8/2003 | Chen .............................. 607/88 |
| 6,615,071 | B1 | * | 9/2003 | Casscells et al. ............ 600/474 |
| 6,671,535 | B1 | * | 12/2003 | McNichols et al. .......... 600/407 |

(Continued)

OTHER PUBLICATIONS

Passe, T. et al., Tumor Angiogenesis: Tutorial on Implications for Imaging, State of the Art, Jun. 1997, vol. 203, No. 3, pp. 593-600.

(Continued)

*Primary Examiner* — Sanjay Cattungal
(74) *Attorney, Agent, or Firm* — Noah J. Hayward (57) ABSTRACT

The present invention relates to methods of passive infrared imaging and dynamic infrared imaging of a tumor or lesion ("DIR") where multiple images are taken before, during and after heating or cooling the tumor or lesion. Patterns of intensity of infrared emission in the infrared image(s) are related to the level of vascularity or metabolic activity of the tumor or lesion, and are used to identify size and shape of the tumor or lesion. The patterns can also be used to determine whether Kaposi's sarcoma lesions, skin cancer lesions and melanomas are active or inactive. Changes in the patterns of infrared emission determined by comparing images taken before, during and after the onset of drug or radiation therapy, are used to assess efficacy of the therapy. The methods can also be used to study tissue affected by angiogenic diseases.

22 Claims, 7 Drawing Sheets

Active Kaposi's Sarcoma Lesion

Optical Image of Lesion
before therapy

Infrared Image Before therapy

Infrared Image After therapy

U.S. PATENT DOCUMENTS

| | | | | |
|---|---|---|---|---|
| 6,881,584 B1* | 4/2005 | Lenhard et al. | | 436/147 |
| 6,975,898 B2* | 12/2005 | Seibel | | 600/473 |
| 7,179,912 B2* | 2/2007 | Halbrook et al. | | 544/106 |
| 7,547,721 B1* | 6/2009 | Miwa et al. | | 514/414 |
| 7,627,365 B2* | 12/2009 | Chance | | 600/475 |
| 2003/0028114 A1* | 2/2003 | Casscells et al. | | 600/474 |
| 2003/0180221 A1* | 9/2003 | Miwa et al. | | 424/9.6 |
| 2003/0208249 A1* | 11/2003 | Chen | | 607/88 |
| 2004/0024390 A1* | 2/2004 | Furumoto | | 606/9 |
| 2004/0236225 A1* | 11/2004 | Murphy et al. | | 600/473 |
| 2004/0267102 A1* | 12/2004 | Skladnev et al. | | 600/315 |
| 2005/0038344 A1* | 2/2005 | Chance | | 600/473 |
| 2005/0197583 A1* | 9/2005 | Chance | | 600/476 |
| 2005/0228291 A1* | 10/2005 | Chance | | 600/476 |

OTHER PUBLICATIONS

Sturesson, et al., Mathematical Modelling . . . , Phys. Med. Biol. (1996), pp. 413-428.

Fiskerstrand, E. J. et al., Therapeutic Response During Pulsed Laser Treatment . . . , Lasers in Medical Science, Nov. 10, 1995, pp. 235-243.

Svaasand, L. O. et al., Tissue Parameters Determining the Visual . . . , Lasers in Medical Science, Nov. 8, 2004, pp. 55-65.

Fader, D. J. et al., Quantifying Postoperative Pain Reduction Using the Dynamic . . . , Arch Dermatol, vol. 136, Nov. 2000.

Imhof, R. E., et al., Photothermal Radiometry for NDE, Progress in Photothermal & Photoacoustic Science and Technology 2, 1993, Elsevier, NY.

* cited by examiner

FIG. 1  Active Kaposi's Sarcoma Lesion

FIG. 1 B Infrared Image Before therapy

FIG. 1 C Infrared Image After therapy

FIG. 1 A

Optical Image of Lesion before therapy

FIG. 2
Active Kaposi's Sarcoma Lesion: Visible & IR 3-5 μm

IR Image 3-5 μm
FIG. 2B

Visible Image
FIG. 2A

FIGs. 3A-3B Mouce Tumor U251 #1

FIGs. 3C-G Mice Tumor G361 #3

Thermal Images: Arm Section Cooled by RT Block

'Rate' Image

A-Magnitude Image

B-Magnitude Image

FIG. 6
Thermal Images: Block Cooled Arm Section

METHOD FOR IMAGING AND SPECTROSCOPY OF TUMORS AND DETERMINATION OF THE EFFICACY OF ANTI-TUMOR DRUG THERAPIES

CROSS-REFERENCE TO RELATED APPLICATIONS

BACKGROUND

1. Field of the Invention

The present invention relates to methods of passive and active dynamic infrared imaging of a tumor or lesion ("DIRI") that heats or cools the tumor or lesion. Patterns of intensity of infrared emission in the infrared image are related to the level of vascularity or metabolic activity of the tumor or lesion, and are used to identify the size and shape of the tumor or lesion. Changes in the patterns of infrared emission determined by comparing images taken before, during and after the onset of drug or radiation therapy, are used to assess the efficacy of the therapy. The methods can also be used to study tissue that has been affected by angiogenic diseases.

2. Description of the Related Art

Tumor angiogenesis, the recruitment of new blood vessels by a growing tumor from existing neighboring vessels, is essential for the growth and persistence of solid tumors and their metastases (Folkman, 1989; Hori et al., 1991; Kim et al., 1993; Millauer et al., 1994). This recruitment of new microvasculature is a central process in tumor growth and aggressive spreading of the tumor through hematogenous metastasis. Angiogenesis depends upon the production of angiogenic factors by host or tumor cells, or both. All solid tumors require angiogenesis for growth and metastasis. Tumors greater than 2 millimeters in size, must obtain their own blood supply; this is accomplished by inducing the growth of new capillary blood vessels. Once these new blood vessels become embedded in the tumor, they provide a means for tumor cells to enter the circulation and metastasize to distant sites such as liver, lung or bone (Weidner, N., et al., The New England Journal of Medicine, 324(1), 1-8 (1991). The level of angiogenesis is thought to be an important parameter for the staging of tumors, and new therapies are being developed which attack the process of angiogenesis for the purpose of attempting to control tumor growth and tumor spread by restricting or eliminating the tumor blood supply. It is therefore of clinical importance to be able to monitor angiogenesis in tumors in a noninvasive manner.

Although angiogenesis is a highly regulated process under normal conditions, many diseases (characterized as angiogenic diseases) are driven by persistent unregulated angiogenesis. Unregulated angiogenesis may either cause a particular disease directly or exacerbate an existing pathological condition. For example, ocular neovacularization has been implicated as the most common cause of blindness and dominates approximately 20 eye diseases. In certain existing conditions, such as arthritis, newly formed capillary blood vessels invade the joints and destroy cartilage. In diabetes, new capillaries formed in the retina invade the vitreous, bleed, and cause blindness. Growth and metastasis of solid tumors are also dependent on angiogenesis (Folkman, J., *Cancer Research*, 46, 467-473 (1986), Folkman, J., Journal of the National *Cancer* Institute, 82, 4-6. (1989).

At present there is no single imaging method capable of providing quantitative characterization of tumor angiogenesis (Passe, et al., Radiology 203:593-600, 1997) or other abnormal angiogenesis. Such a method would facilitate monitoring the efficacy of antiangiogenesis factors for therapeutic use, tumor staging, and diagnosis of angiogenic diseases.

SUMMARY OF THE INVENTION

The present inventions provide methods for determining the activity of a tumor or lesion using IR imaging. In a first aspect this method includes obtaining an IR image of the lesion at a specific orientation at a first time, obtaining an optical image of the lesion at a second time that is close to the first time at substantially the same specific orientation, comparing the IR image and the optical image to determine the relative size and perimeter of the lesion, and determining that the lesion is active if at least one of the size and the perimeter of the lesion in the IR image is significantly larger than the size and the perimeter of the lesion in the optical image, respectively. In another aspect a method is provided for determining the activity of a Kaposi's sarcoma lesion having an observable pigmented area using IR imaging, including obtaining an IR image, examining the IR image to determine if a size and a perimeter of the pigmented area can be identified in the IR image, if the size and perimeter of the pigmented area can be identified, then comparing the size and perimeter of the pigmented area to the size and perimeter of a thermal image of the area in the IR image, and determining that the area is active if the size and perimeter of the thermal image is significantly larger than the size and perimeter of the pigmented area, respectively.

Another apsect is determining the efficacy of therapy of a cancerous mass using IR imaging, by obtaining a first IR image of the mass at a specific orientation at a first time before or during the course of therapy, obtaining a second IR image of the mass at the specific orientation at a second later time during the course of therapy, comparing the first and second IR images of the mass to determine their relative sizes, and determining that the therapy is effective if the second IR image of the mass is smaller than the first IR image of the mass. The therapy can be drug or radiation therapy.

Another aspect is a method for determining a characteristic of a tumor or lesion, by obtaining a first infrared image of the tumor or lesion and the surrounding tissue at a first time at ambient temperature, identifying a first pattern of infrared emission in the first infrared image, heating or cooling the tumor or lesion and the area of tissue surrounding the tumor or lesion to a desired temperature, obtaining a second infrared image of the tumor or lesion and the surrounding tissue at the desired temperature, identifying a second pattern of infrared emission in the second infrared image, comparing the first and second patterns of infrared emission to determine differences in infrared intensity between the first and second patterns of infrared emission, and characterizing the tumor or lesion based on the differences in infrared intensity between the first and second patterns of infrared emission. In this method the tumor can be heated or cooled and the differences in infrared intensity between the first and second patterns of infrared emission characterize the tumor or lesion based on vascularization or metabolic activity.

In another aspect the method is for determining a characteristic of a tumor or lesion, by heating or cooling the tumor or lesion and an area of tissue surrounding the tumor or lesion to a desired temperature, removing the heating or cooling source, obtaining a first infrared image of the tumor or lesion and the surrounding tissue at a first time after removing the heating or cooling source, identifying a first pattern of infrared emission in the first infrared image, repeating step c at a second time after removing the heating or cooling source to obtain a second infrared image, identifying a second pattern of infrared emission in the second infrared image, comparing the first and second patterns of infrared emission to determine differences in infrared intensity between the first and second patterns of infrared emission, and characterizing the tumor or lesion based on the differences in infrared intensity between the first and second patterns of infrared emission.

The invention also provides a method for determining the extent of vascularization of a mass using infrared imaging, comprising obtaining an infrared image of the mass, determining areas of higher than average infrared emission, and associating the areas of higher than average infrared emission with vascularization of the mass.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 shows an optical (FIG. 1A) and an infrared image (FIG. 1B) of an active Kaposi's sarcoma lesion before electron beam therapy and of the active Kaposi's sarcoma lesion after electron beam therapy (FIG. 1C).

FIG. 2 shows an optical image of an active Kaposi's sarcoma lesion (FIG. 2A) and of the same lesion using IR imaging (FIG. 2B).

FIG. 3E is an infrared image of the human melanoma G361 #3 before microwave heating, after 60 seconds of exposure to microwaves (FIG. 3F), and 60 seconds after the end of the microwave exposure (FIG. 3G).

DETAILED DESCRIPTION

The present invention is directed to a method of determining regions of vascularity and higher than average metabolic activity of a tissue, tumor or lesion using infrared ("IR") radiometric thermal imaging. Information on the extent of vascularization and the amount of metabolic activity obtained from IR images taken before and at one or more times after the onset of drug therapy, can be used to assess the efficacy of anticancer or angiogenic disease treatments with drugs or radiation. Because tumor angiogenesis is vital to tumor survival and growth, information on changes in tumor vascularization is useful to monitor efficacy of any treatment, including treatment with antiangiogenesis factors or other regimen that directly or indirectly affects tumor growth.

The invention is described in part with reference to specific embodiments thereof. It will, however, be evident that various modifications and changes may be made to the inventions without departing from the broader spirit and scope of the invention. The present application also includes several non-limiting examples.

Angiogenesis is essential for normal body activities including reproduction, development and wound repair. Although the process is not completely understood, it is believed to involve a complex interplay of molecules, which regulate the growth of endothelial cells (the primary cells of capillary blood vessels). Under normal conditions, these molecules appear to maintain the microvasculature in a quiescent state (i.e. one of no capillary growth) for prolonged periods which may last for as long as weeks or, in some cases, decades. When necessary (such as during wound repair), these same cells can undergo rapid proliferation and turnover within a 5 day period (Folkman, J. and Shing, Y., The Journal of Biological Chemistry, 267(16), 10931-10934, and Folkman, J. and Klagsbrun, M., Science, 235, 442-447 (1987).

To stimulate angiogenesis, tumors upregulate their production of a variety of angiogenic factors, including the fibroblast growth factors (FGF and BFGF) and vascular endothelial cell growth factor/vascular permeability factor (VEGF/VPF). However, many malignant tumors also generate inhibitors of angiogenesis, including angiostatin and thrombospondin. It is postulated that the angiogenic phenotype is the result of a net balance between these positive and negative regulators of neovascularization.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Angiogenesis has also been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site. Kaposi's sarcoma is an example of a cancerous tumor that is highly vascularized.

The development of cancer beyond extremely small lesions (100 to 180 microns) is dependent on the growth of new blood vessels (neovascularity) into the tumor to supply oxygen and nutrients. The extent of this neovascular growth and the correlated limitations on the extent of oxygenation and nutrition is an important factor in characterizing and treating the tumor. Specifically, the extent of the vascularity impacts the growth rate of the tumor, the susceptibility of the tumor to metastasis and the response of the tumor to therapy, particularly radiotherapy. Thus measuring the pattern and efficiency of vascularity of tumors is an important factor in the management of malignant disease. While there are established methods for measuring the pattern of vascularity in tumors, for instance using anigography and PET scanning, these methods are expensive and invasive. They require injections of radio-opaque dyes or specific agents that serve as a physical marker for blood vessels.

Temperature is another property of tumors that is related to blood flow. The temperature of tumors can be altered by changes in the temperature of surrounding normal tissue due to several factors. First, tumors or lesions containing more blood vessels than normal tissue (hypervascular lesions) will have an elevated temperature compared to normal tissue. Kaposi's sarcoma is an example of this type of lesion. Most solid tumors, however, have fewer active blood vessels and hence are hypovascular compared to normal tissue which makes them cooler than the surrounding tissue environment. The actual difference in temperature can result from one of several mechanisms. First, warm blood from the core of the body heats all tissue above ambient temperatures through convection and conduction. Reduced vascular density or reduced blood flow in vessels can reduce temperature toward ambient temperature. Second metabolic processes in cells and tissues attendant to homeostasis is an exogenic process that provides heat, although generally the heat generated by this mechanism is small compared to conduction and convection from blood vessels. The maintenance of the core body temperature is an extremely important mechanism for warm-blooded mammals and multiple mechanisms exist by which the flow of blood to the parts of the body, particularly the skin, can be reduced or enhanced. These mechanisms are vasoconstriction and vasodilation, which work to prevent excessive warming or cooling of the body core. One important structural difference in the muscular component of blood vessels in normal tissues and blood vessels in tumors is that tumor neovasculature cannot respond to local or sympathetic signals to undergo vasoconstriction and vasodilation. Indeed the absence of these processes in tumors has been a target for improving radiotherapy and chemotherapy.

Many investigators have attempted to use infrared radiance to monitor temperature for medical purposes. Anatomical studies have shown that there is a positive correlation between the extent of neovascularization of the primary tumor in breast cancer and the rate of recurrence. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly decrease recurrence of the tumors. Positron emission tomography (PET) studies have also been reported that show increased blood flow in breasts containing malignant lesions, compared to the contralateral normal breast.

A group at Ville Marie Medical Center under the direction of Dr. John Keyserslingk has focused on what is herein referred to as passive IR imaging for early breast cancer detection. In their studies, single IR images acquired at various times (typically separated by many months) were used to identify changes in IR emittance over time before and after surgery and chemotherapy. They looked exclusively for asymmetric emittance patterns between the two breasts. Such asymmetry is assumed to indicate the presence of a lesion based on empirical correlation of IR observations with subsequent identification of lesions using mammography or other direct diagnostic procedures. The enhanced IR signature seen in the cases studied is postulated to originate from changes in breast vascularity. However, there is no information on how deep in the breast is the source of the IR emission. In fact, tumor-induced changes in surface vascularity are inconsistent with current concepts of chemotaxic and tumor induced angiogenesis. The result is that the current methods of IR imaging produce interesting images that cannot be interpreted using existing analysis methods and hence such IR imaging cannot be considered an independent procedure for tumor diagnostics.

According to embodiments of the invention, methods that use perturbation of the steady-state pattern of temperature in tumors and normal tissue result in improved imaging of differences in infrared irradiance. This approach uses Dynamic Infrared Imaging (DIRI) to resolve changing infrared irradiance after cooling or heating into basic parameters that describe the actual heat transfer processes. This approach not only presents improved images contrasting patterns of difference in IR irradiance, but it offers the power to study the mechanisms by which normal and malignant tissue differ in response to perturbed temperature. Observations show that this methodology can be used to 1) identify both hypervascular and hypovascular tumors and lesions, 2) offer new approaches to staging disease by characterizing heat transfer processes within the tumor or lesion, and 3) identify the differential contribution of vasoconstriction and vasodilation to heat transfer. DIRI of dermal tumors or lesions and those that are accessible to endoscopy: 1) enhances detection of small tumors, 2) provides a basis for staging tumors based on small scale patterns of vascularity, and 3) measures immediate and delayed response or the absence of a response of tumors to different therapies. In studies reported below DIRI was used to study mouse xenografts of glioblastoma and melanoma. Embodiments of the invention provide a mechanistic basis that can measure the underlying processes. This in turn, allows a completely non-invasive process for screening for early signs of breast cancer lesions that are within 100 microns of the surface, or that have properties that alter surface IR irradiance. In other embodiments, passive IR imaging conducted without actively heating or cooling to manipulate local temperature, is used to diagnosis and distinguish tumors or lesions within 100 microns of the surface (like KS, basal cell carcinoma or melanoma), or that have properties that alter surface IR.

Results of applying embodiments of the invention are described in the following sections. To underscore the results some explanations are provided based on theoretical considerations. However, this invention is not limited by any particular theory.

I. Passive IR Imaging

Blood vessels that actively transport blood are an internal heat source that emits IR radiation at higher rates than the surrounding tissue. It has now been discovered that passive infrared radiometric thermal imaging of tissue, tumors or lesions that are located on or within about 100 microns from the surface being imaged, provides a noninvasive technique to assess and monitor the extent of vascularization. Because tumor angiogenesis is vital to tumor survival, measuring the extent of tumor vascularization provides another means of grading or staging a cancerous tumor or lesion. Monitoring changes in tumor vascularization using IR imaging over time before or after the onset of therapy is also a valuable new tool for assessing efficacy in treating cancers such as Kaposi's sarcoma, basal cell carcinoma, and melanoma. There has been a concerted effort to design and identify drugs that specifically interfere with tumor neovascularization, called antiangiogenesis factors, for use as chemotherapeutic agents. Antiangiogenesis factors are also useful in treating angiogenic diseases. The use of IR imaging of lesions or in in vivo or in vitro model systems will greatly speed up the discovery and screening of antiangiogenesis factors and anticancer drugs that directly or indirectly decrease tumor vascularization.

Passive IR imaging measures the IR radiation emitted by a body or tissue that is heated above ambient temperature; the excess heat correlates with elevated metabolic activity. Highly vascularized tissue typically emits IR radiation at higher rates than surrounding tissue with less vascularization. Initial studies were conducted on AIDS patients with Kaposi's sarcoma (KS) where infection by the Human Herpes virus type 8 (HHV8) plays a major role in the pathogenesis of the disease. In this country, most of the cases of KS are epidemic, affecting mainly men who have sex with men, and who are coinfected with the Human Immunodefficiency virus (HIV). Kaposi's sarcoma is a neoplasm of endothelial cells with lesions that are often located on or near the epidermis. KS frequently affects the skin and mucous membranes alone or in association with systemic involvement. Internal disease is commonly seen with lymphatic, respiratory and/or gastrointestinal involvement or some combination, causing asymptomatic or symptomatic disease and even progression to death from complications. Patients develop one, a few or multiple lesions on the skin that can be localized, grouped, symmetrically distributed or generalized. The most common types of skin lesions are the patches and plaques, but nodules and exophytic tumors with ulceration can also be present. It is now know that the lesions represent a neoplastic proliferation of spindle-shaped undifferentiated endothelial cells forming unstructured vascular spaces, which are usually filled with blood. Blood is also extravasated to the interstitial spaces between cells causing the purplish brown color typically seen in KS lesions.

Initial evaluation of the extent of cutaneous involvement by KS is often complicated by the infiltrative nature of some of the lesions, which may have ill-defined borders that are poorly palpable and that do not correspond to the limits visible on the skin surface. When cutaneous KS is successfully treated, the skin lesions become even more ill defined, with barely palpable borders. The discoloration may persist indefinitely. Currently, it is very difficult to make a definitive diagnosis of KS lesions without biopsy and histologic analysis of previously treated lesions. This is because visible dyspigmentation can represent a residual (inactive) lesion, such as residual hemosiderin deposition where the disease is inactive, or it can indicate an active KS patch-type lesion, where there are patent vascular spaces and endothelial cell proliferation. Non-invasive techniques and parameters are needed to aid in the initial evaluation and follow-up of patients affected by cutaneous KS.

A. Method of Monitoring Tumor Vascularization in Kaposi Sarcoma Lesions Using Passive Infrared Radiometric Thermal Imaging KS lesions are planar, near-surface and hyper-vascular lesions. In one embodiment for imaging KS lesions, IR emittance over the mid-infrared wavelength band from 3-5 micrometers (3,000-5,000 nanometers) was monitored using an infrared focal plane array camera with a cold filter and a warm filter for wavelength selection in the band from 1 micrometer to 5.3 micrometers. However, wavelengths ranging from about 2.5 micrometers to about 30 micrometers can be selected in other embodiments. Cameras operating in other wavelength bands can also be used in other embodiments, depending on the application and where, for example, dyes have been used to augment emission. The IR measurement system used in the illustrated embodiment also included a visible, color charge coupled device (CCD) to obtain coordinated visual optical images, and an active registration system that permits visible and infrared images of tumors to be registered for purposes of identifying the location of features seen in each. One embodiment of such active registration system is a set of four laser diodes positioned in a square array wherein the laser light beams are parallel to each other and strike the sample at the same spacing on the patient that existed on the array.

Tissue is not highly absorbing in the infrared. This means that infrared radiation that is emitted from metabolically active vascularized tissue, for example, will pass through the surrounding and overlying tissue for some distances without being absorbed. This permits detection of IR emitted energy using non-invasive IR imaging. The net IR emission and its wavelength response depends on the depth and lateral distribution of the vascular growth in the tumor, associated metabolic activity, and optical properties of the tumor and surrounding tissue (including the tissue located between the tumor and the skin surface).

IR and visible images of approximately ten KS lesions in each of five different patients were made. FIG. 1 is an example of an active KS lesion with IR images taken before and after electron beam treatment; and FIG. 2 is an example of active KS lesions in a different patient. All related figures are set to the same scale and they correspond in position and magnification to enable accurate comparison of size and shape.

Figure 1A:
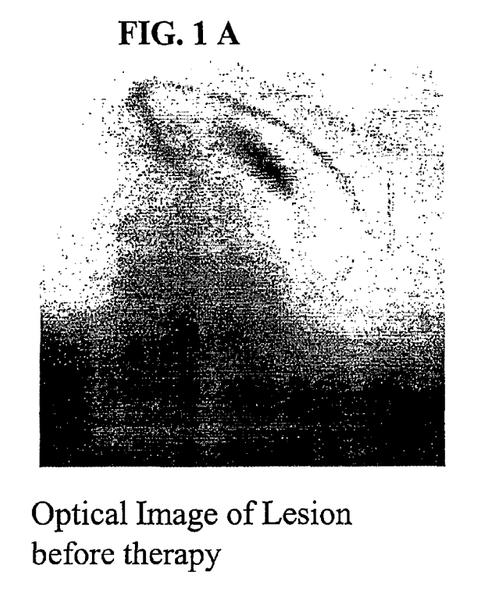
Figure 1B:
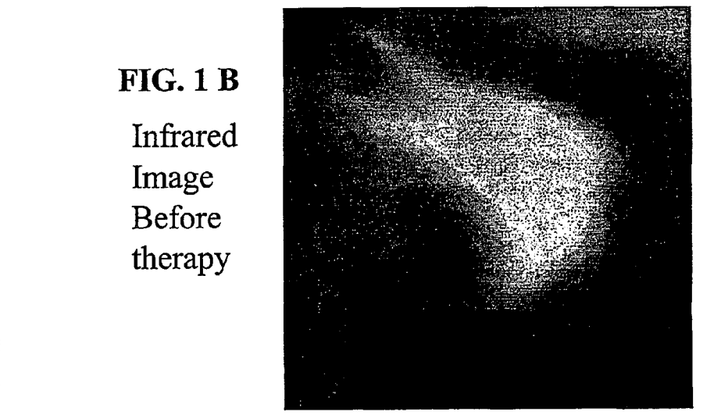
Figure 1C:
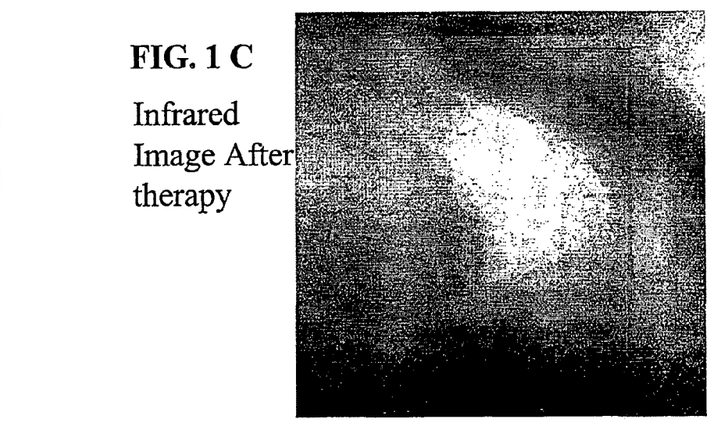

FIG. 1A is an optical image of a KS lesion taken before electron beam therapy. The dark ring represents the periphery of the visible image of the pigmented lesion. FIG. 1B is an IR image taken at the same time and at the same position as FIG. 1A, and FIG. 1C is an IR image taken after electron beam therapy. The apparent size of the lesion in the visible image in FIG. 1A is noticeably smaller than in the corresponding IR image in FIG. 1B. FIG. 1C shows a significant reduction in the size of the IR image of the lesion in response to electron beam therapy which, when effective, causes necrosis of the microvessels in the lesion. While the post-therapy IR image (FIG. 1C) showed a decrease in size compared to the pre-therapy IR image (FIG. 1B), the optical images before (FIG. 1A) and after therapy (not shown) were unchanged. The difference in size of the optical image and the larger IR image taken before therapy is due to the IR emittance from patent, viable blood vessels in and at the periphery of the lesion. A reduction of the size of the IR image following electron beam therapy is taken to be due to necrosis of a portion of the blood vessels at the periphery of the lesion. The IR images of the KS lesion in FIGS. 1B and 1C also show features that resemble processes extending outward from the nominal edge of the lesion that are not present in the visible image. These processes may mark areas of induced proliferation of blood vessels from the surrounding tissue, i.e. sites of angiogenesis. In all of the active lesions observed, the infrared image size was at least equal to or greater than the visible image size. The perimeter of the active lesion was likewise equal or greater than that of the corresponding optical image, and typically showed an irregular periphery compared to the visible image.

Figure 2A:
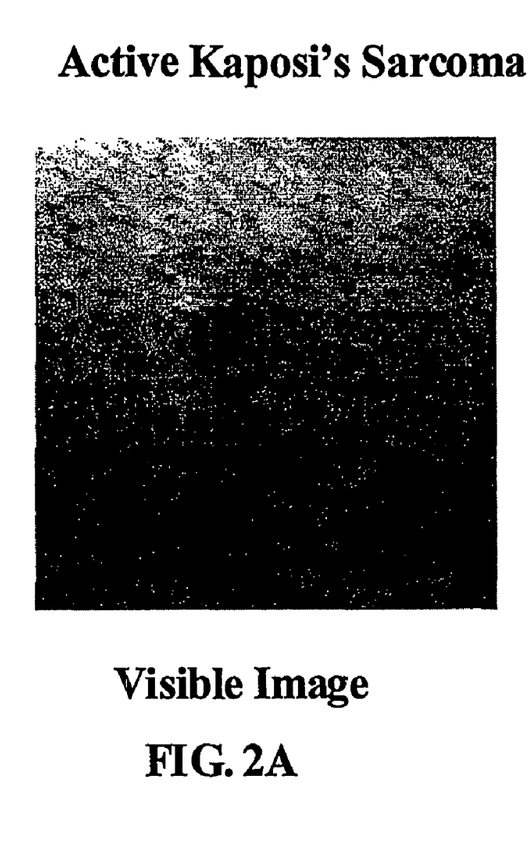
Figure 2B:
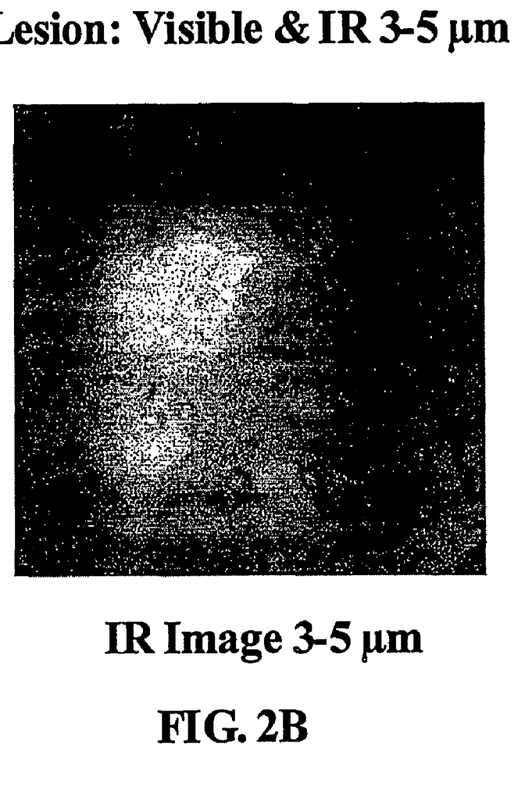

FIG. 2 shows another pair of optical and infrared images of active KS lesions using passive IR imaging in a second patient. In this case, the visible optical image in FIG. 2A shows a single roughly spherical pigmented lesion. However, the IR image in FIG. 2B reveals the presence of two active lesions as noted by the elevated temperature shown by the brighter center in the two lesions. The active lesions in FIG. 2B show a different morphology than the lesion in FIG. 1B, which had brightly imaged vascular processes proceeding from the periphery. By contrast, the lesions in FIG. 2 are more regular and are more circular in shape. The two lesions may be different types of KS tumors. Further and more detailed information on the size and shape, vascularization and metabolic activity of a mass or tissue can be accomplished using DIRI, which is discussed below. Information obtained with DIRI permits more accurate classification and staging of the tumors than is available using optical images only or passive IR imaging.

Changes in IR images become evident early in the treatment process, as is evidenced by the observation that a single electron beam treatment caused a decrease in vascularization of the KS lesion (FIG. 1). Changes in angiogenic or metabolic activity resulting from drug therapy may be detectable early in the course of treatment, thereby reducing the time required to assess efficacy of treatment in a given individual, and permitting assessment of efficacy on an individual-by-individual basis. Large variations in the IR images among different KS lesions in a single individual were observed, while variations in the corresponding visible images were small. This variability in size is due to the extent of vascularization of individual KS lesions. Some variability also results because many types of skin tissue are partially transparent in the infrared allowing greater escape of emitted radiation from subsurface regions.

In one embodiment of the invention passive IR imaging is used to determine the activity of a mass such as a tumor or lesion, by comparing the size and shape of a visible image of the lesion to an IR image of the lesion taken at approximately the same time and with the same orientation. If the IR image of the lesion is larger than the corresponding optical image, then the lesion is an active lesion with viable blood vessels transporting blood (hence heat) to the surface, or with a high level of intrinsic metabolic activity that generates heat. Alternatively, if the IR image of the lesion is smaller than the corresponding optical, then the lesion is inactive. A further indication of an active lesion is if the border of the IR image is irregular or has processes extending from it, compared to the optical image. An IR image of an inactive lesion would be typically be smaller than the corresponding optical image, and would typically have a perimeter that corresponds relatively closely to the perimeter of the optical image.

In another embodiment, a determination of lesion activity can be made using IR imaging alone, without obtaining an optical image for comparison. This works in cases where the perimeter of the lesion is visible in the IR image. In that case, one can determine that the lesion is active if the IR image of the lesion is larger than the border of the visible image of the lesion. Pigmented lesions such as KS and melanoma are visible in an IR image.

The present invention also provides a method for determining the efficacy of therapy with drugs or radiation, of tumors or lesions such as KS, basal cell carcinoma and melanoma, or of cancers accessible by endoscopy. In this embodiment, an IR image is taken before or soon after beginning therapy, and again at one or more later times after initiating therapy. A decrease in the size of the IR image over time after beginning therapy should be an indication that the therapy is effective. Efficacy can be achieved by decreasing tumor neovascularization or metabolism, or by other mechanisms. The therapy thus monitored includes drug or radiation therapy with x-rays, thermal radiation, microwaves, or ultrasound. IR emission from tumors that lie within about 100 microns of the surface can be monitored directly. This permits study of changes in vascularization or metabolic rate of the mass before, during and after treatment with potential antiangiogenesic and carcinogenic agents.

IR imaging is a non-invasive method for determining efficacy of treatment and permits individualization of treatment with rapid determination of efficacy in designing and screening new drugs that directly or indirectly affect tumor or tissue vascularization or metabolism. Imaging studies based on passive infrared imaging of temperature changes is useful for assessing diseases characterized by alterations in the structure or function of skin vasculature or vascular proliferations such as malignant or benign vascular tumors and melanomas, or angiogenic diseases.

Kaposi's sarcoma is a true endothelial cell neoplasm with increased blood pooling and consequent increased local temperature and IR emittance. IR thermography is therefore a very useful tool to assess the extent of initial cutaneous involvement, to grade therapeutic response, to evaluate on an individual-by-individual basis the efficacy of drug therapy, and possibly to predict recurrences of the disease early in the process. Imaging software can be used to facilitate comparison of optical and IR images with one another, and to measure the relative size, shape and orientation of the images of the lesion.

Some antiangiogenesis factors currently known or under development for use in treating angiogenic diseases, include Suramin, retinoids, interferons, antiestrogens, protamine vinblastine, endostatin, paclitaxel and its analog docetaxel, heparin, certain steroids such as tetrahydrocortisol, 4 kDa glycoprotein from bovine vitreous humor and a cartilage derived factor, human interferon beta, human recombinant a interferon (alpha/A), ascorbic acid ethers and related compounds, sulfated polysaccharide DS 4152, a fungal synthetic fumagillin and O-substituted fumagillin derivatives, platelet factor, interferon-alpha, interferon-inducible protein, and the 16 kDa N-terminal fragment of prolactin. The only known angiogenesis inhibitor that specifically inhibits endothelial cell proliferation is angiostatin.

Diseases such as chronic inflammation may also involve pathological angiogenesis that can be staged or diagnosed by IR imaging. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis where the plaques formed within the lumen of blood vessels have been shown to have angiogenic stimulatory activity. One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use. The methods of passive IR imaging and DIRI of the present invention may help develop new drugs and determine which drugs a given individual responds to.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula. Advanced diabetes is also frequently accompanied by abnormally high vascularization of the eye that interferes with vision and in the extreme case can cause blindness. The methods of IR imaging described herein can be used to diagnose angiogenic diseases and monitor therapy.

II. Dynamic IR Imaging with Active Extrinsic Heating or Cooling

In another aspect of the invention, a new dynamic infrared imaging technique (hereafter "DIRI") that involves active heating or cooling of a mass or tissue, permits detailed analysis of living tissue, including abnormal tissue, to identify regions of modified metabolic activity associated with increased infrared. An example of a high activity region is an area where active angiogenesis promotes tumor growth. An example of a region of low activity is an area of reduced perfusion due to impaired peripheral circulation such as is common in advanced diabetes, especially in the legs and feet.

Controlled changes in the infrared emittance signature of a sample, e.g. the tissue or tumor, can be intentionally produced by changing the sample temperature using active heating or cooling. Sources of cooling or heating cause spatial and temporal changes in the IR image that in turn are used to infer internal structure. When the surface of the tissue to be imaged is actively cooled, both surface and internal temperature of the tissue begin to change by thermal diffusion with the temperature varying as the square root of time at a given depth. The magnitude of the temperature change at a given depth is also a function of, and hence affected by, any heat sources that may be present in the tissue such as areas of high metabolic activity or high blood flow. Spatial-temporal changes in sample (tissue) temperature modify the IR emittance from the sample. Thus analysis of the IR radiometric profile at specific wavelengths allows the temperature profile to be monitored as a function of time. There are a number of special cases that are relevant to tumor characterization.

A. Tissue Vaso-Processes (Vasoconstriction or Vasodilation of Small Vessels)

According to the bioheat equation, blood flow transports heat at time scales that are faster than thermal diffusion. Thus, there is a difference between heat transport around an area that is actively heated or cooled, and around regions that are not subject to the thermal challenge, such as the interior of the body that is far away from the applied heat or cold source. Vasoconstriction is the narrowing of blood vessels, which produces less heat transport to a region of tissue. Vasodilation increases blood flow and hence heat transport to a region of tissue. Vasoconstriction and vasodilation are under both local and sympathetic nervous system control. However, neovascular blood vessels such as are in a tumor or lesion are thought not to be subject to these neuronal controls. Therefore, active cooling of an area leads to vasoconstriction in normally vascularized tissue resulting in a decrease in heat transport and a rapid decrease in local temperature. By contrast, a tumor presented by the same cold challenge will not experience as rapid a decrease in temperature as the surrounding vascularized tissue because the neovascular blood supply of the tumor is not under local or sympathetic control. Therefore, the result is that the tumor that does not undergo vasoconstriction has a higher temperature relative to the surrounding tissue, which enhances its visibility using IR imaging.

After removal of the cold source, the vasoconstriction stops and the temperature of the surrounding tissue rises quickly. By contrast, after the cold source is removed, the temperature of the tumor will change slowly principally by thermal diffusion, which varies as the square root of time at a given depth, thus permitting measurement of spatial-temperature profiles that infer structure of the vascularization of the tumor or lesion.

B. Tumor Metabolic Processes

The bioheat equation also describes the contribution of local metabolic processes to local temperature. Temperature is a measure of the quantity of internal energy present within a sample volume. This quantity of internal energy is modified by processes of energy production within the volume and by transport into the volume from surrounding regions or from external heat sources absorbed within the volume. The metabolic processes within an actively growing tumor or at its boundary with surrounding normal tissue are rapid, resulting in additional local thermal energy production. An example of such a process is angiogenesis through which a tumor grows by subverting normal tissue and promoting vascular growth into the tumor to sustain tumor processes. Hence whether through metabolism or through additional blood flow, the result is that the boundary of the tumor and normal tissue is a region-of-increased temperature that is detectable using IR imaging.

C. Active Source Heating

Any external source that deposits energy within a volume of tissue causes a local increase in tissue temperature and hence increased emittance. One example of application of energy to facilitate tumor characterization is based on the observation that near-infrared light at wavelengths of about 720 and 640 nanometers is selectively absorbed by deoxyhemoglobin and oxyhemoglobin, respectively. Such selective absorption is therefore able to identify and distinguish regions with high oxygen concentration such as areas of increased neovascularization at the boundaries of actively growing tumors. Irradiation with IR light in the 640 and 720 nm wavelength range can provide additional information to supplement the information provided by thermal diffusion from the surface. Such selective heating by an optical source is an example of a more general functional imaging approach using electromagnetic sources ranging from x-rays to microwaves.

In all three cases, targeted subsurface regions are directly visible if the IR radiation they emit can reach the imaging camera. The depth in tissue where this is possible varies with wavelength, but as described previously is at best of the order of several millimeters below the surface. However, internal heat production deeper within the tissue, for example from metabolically active, highly vascularized tumors, also produces temperature changes in regions that are closer to the surface and are hence within the range of IR detection. The result is that IR imaging can be used to detect areas of increased metabolic activity and vascularization in tumors that are located much deeper within the tissue than the infrared emission depth. To illustrate this effect, consider a tumor that generates heat due to increased neovasculariziation, higher than average blood flow and rapid cell proliferation, which tumor is covered by normal less vascularized and less active tissue. When viewed by an IR camera, the presence of the tumor is readily detected (albeit as a blurred image) because of the increased IR radiation emitted from the overlying tissue near the surface whose local temperature (above the tumor) is increased relative to surrounding regions of overlying tissue due to heat diffusion and transport from the interior tumor. If the temperature of the tumor is further temporally modulated using an external hot or cold source applied at time $t_0$, then the time course of the emitted radiation as a function of elapsed time, $t-t_0$ (monitored by taking sequential IR images at various times during heating or cooling and after removal of the hot or cold source) can provide information on tumor depth and on the thermal properties of the overlying tissue, as well as the lateral position.

The general conclusion is that passive infrared imaging is enhanced and made more quantitative by taking a series or sequence of IR images following stimulation with actively controlled sources, which include surface cooling in combination with selective active heating by temporally or spatially modulated sources. One specific temporal modulation in some embodiments of the invention is step function heating. Other modulation waveforms can also be used in other embodiments. An advantage of step heating when used with surface cooling and tissue cooling through diffusion is that the time scale can be matched to diffusional times in tissue. Such diffusional times are approximately given as $\tau_d = d^2/\alpha$ where d is the depth and $\alpha_T = 0.0015$ cm$^2$sec$^{-1}$ is the thermal diffusivity of tissue. For d=0.1 cm, $\tau_d$=6.6 seconds.

Time sequenced IR imaging has been used to characterize various engineering materials including composites, coatings and bonded structures. It has also been used to a limited extent to characterize normal skin for applications in dermatology including treatment of port wine stain and penetration of various topically applied emoluents. In some cases this work has sought to characterize the internal temperature profiles produced by laser or other optical heating. Sturesson, C. et al., Phys. Med. Biol. 41: 413-428 (1996), Fiskerstrand, E. J. et al., Lasers in medical Science, 12: 320-327 (1997), Fader, D. J., Arch. Dermatology 136:1416 (Nov. 2000), Imhof, R. E. et al "Photothermal Radiometry for NDE" in Progress in Photothermal & Photoacoustic Science and Technology 2, (A. Mandelis ed.) Elsevier, N.Y. 1993. While some work has been done to characterize infrared transparent materials such as skin, it is very limited. Even less has attempted to identify and characterize internal heat sources associated with metabolic processes or with changes in perfusion and none focused on functional imaging. According to an embodiment, thermal diffusion analysis using DIRI includes responses over time to cold challenge in a partially transparent skin medium, which is a new development that is described in more detail below. DIRI is applicable to characterization of tumors and lesions and to both diseased and normal tissues. DIRI images of the surface directly monitor short time changes in near-surface vasculature. They can be indirectly linked to deep tumors such as those of the breast, as will be discussed below.

DIRI also provides additional structural information about tumor angiogenesis and tissue vascualrization. Detailed comparison of both single image frames in the visible and infrared wavelengths, and of sequential sets of images obtained under ambient conditions and under cold and heat challenge, can reveal additional structural information that is useful for diagnosis and staging of tumors. Sequential images taken under dynamic, changing temperature conditions will reflect changes in image intensity with time and position within and around the tumor. Through study of this spatio-temporal response temperature gradients internal to the tumor or lesion as a function of time are determined, and information on tumor depth and the location of localized internal heat sources (areas of high metabolic activity) associated with internal metabolic processes are derived. Analysis of time sequences of DIRI images provides information on internal heating rates and thermal transport through the time dependence of the IR radiance (emission). The result provides a kind of functional image of the tissue, tumor or lesion instead of a purely dimensional image. For example, for KS, the expected differences in temperature for normal vasculature and for abnormally increased endothelial cell proliferation in active KS lesions can be quantified to provide a new method for assessing subcutaneous activity and the extent of involvement.

It should be noted that temperature is a convenient but inexact description of the radiance distribution emanating from the tissue since in the present case of partially transparent media such as skin, the radiance is an integral over depth weighted by internal reabsorption and scattering in the infrared wavelength bands.

Figure 3A:
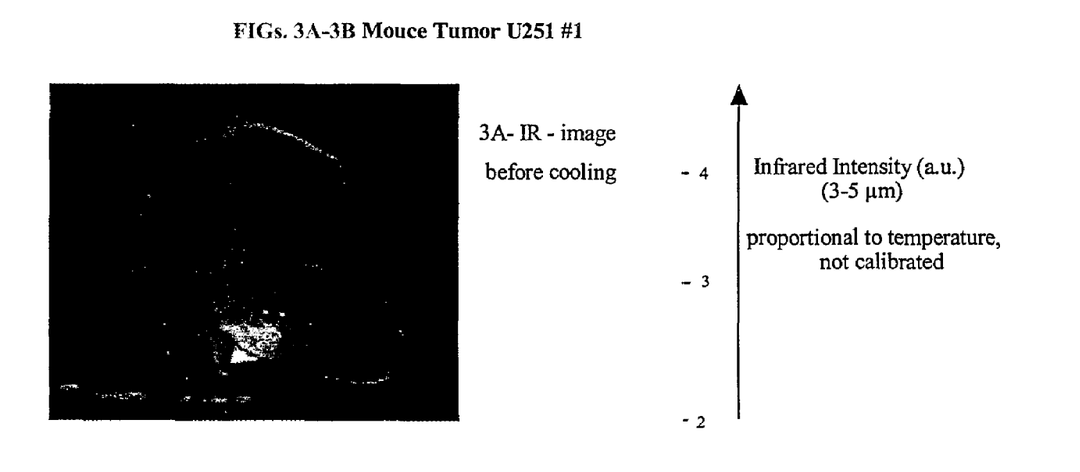
FIG. 3A and FIG. 3B are infrared images of mouse xenografts of human U251 #1 glioblastoma cells before cooling (FIG. 3C) and at different times after initial cooling (FIG. 3B).
Figure 3B:
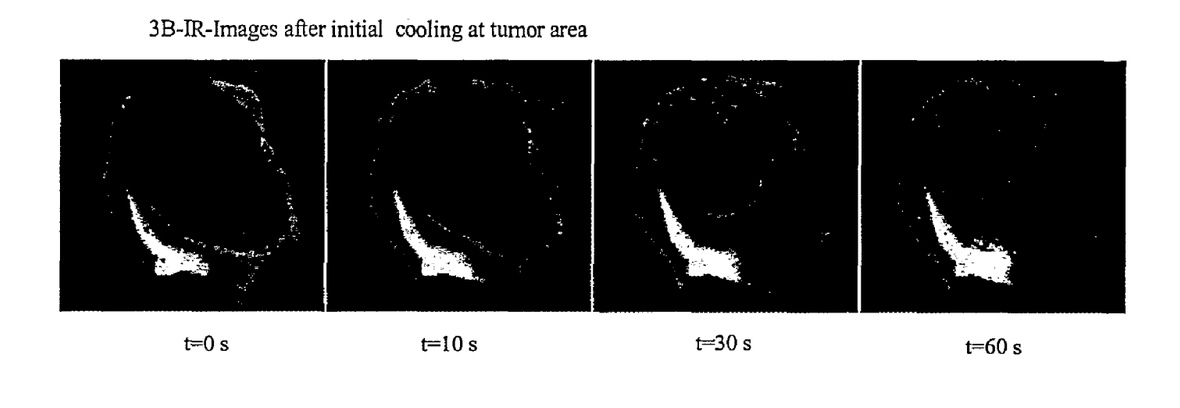

D. Method of Visualizing Tumors in Xenografts of Human Glioblastoma Cells and Human Melanoma Using DIRI FIG. 3A and FIG. 3B show the IR profile of a xenograft comprised of U251 #1 human glioblastoma cells grafted onto a nude mouse before cooling (FIG. 3A), and at various times after cooling (FIG. 3B). IR intensity is proportional to temperature. The yellow area represents the area of highest temperature. The green area radiates less heat than the yellow area, but more heat that the dark blue area. The light blue color represents an area of transition from green to dark blue. The purple areas represent the coolest areas at room ambient temperature.

The IR emission patterns show selective spatial-temperature recovery that indicates areas of active and inactive vascularity. Before cooling, the IR image does not clearly distinguish the glioblastoma from the healthy tissue in FIG. 3A. There appears to be a gradient from a lower temperature at the outer edge of the tissue to a warmest spot at the lower central portion of the tissue. However, a second IR image taken at time t=0, after the tumor and surrounding tissue have been cooled, the tumor appears as a well delineated purple mass that has a sharp outline compared to the image taken before cooling. At a third later time after the cooling source is removed, vascularized areas recover first because the flow of blood carries heat faster than heat can diffuse from warmer areas to cooler areas. The tumor begins to warm first at the periphery and warms increasingly toward the interior of the tumor over time. The purple to yellow time progression indicates the greatest extent (or border) of the tumor is visible in the IR image taken at time t=0. The results in 3B also show that the necrotic center is displaced above and to the left of the geometric center of the tumor. Glioblastomas are very resistant to radiotherapy, therefore using DIRI will be very important to identify new therapeutic regimens.

Figures 3C, 3D:
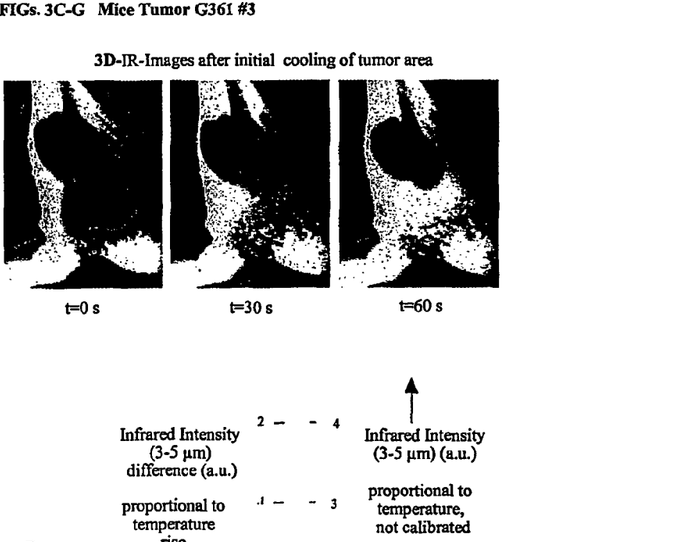
FIG. 3C and FIG. 3D are infrared images of mouse xenograft of human melanoma G361 #3 before cooling (FIG. 3C) and at different times after initial cooling (FIG. 3D).
Figure 3C:
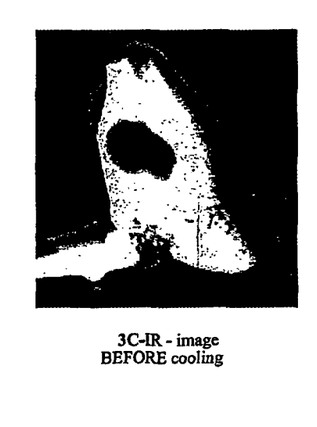

FIGS. 3C-G show a mouse xenograft of human melanoma G361#3 before and after cooling and heating. FIG. 3C shows an IR profile of the melanoma before cooling; FIG. 3D shows IR images taken at various times after cooling (FIG. 3D). As in the case of the human glioblastoma, the melanoma is not well differentiated from the surrounding tissue in an IR image of the tumor taken at ambient temperature before the melanoma is perturbed with heating or cooling. In FIG. 3C the melanoma appears as a single lobe of warmer (green) tissue before cooling. However, DIRI shows that after the melanoma and surrounding tissue are cooled, the tumor appears purple at t=0 (FIG. 3D), and clearly has two distinct lobes. After the cooling source is removed, the lobes warm, which is evidenced by the transition from purple to green and yellow. As is the case with glioblastoma, the center of the melanoma tumor is the coolest. The sequential melanoma images in FIG. 3D taken at various times (t=0, t=30 sec and t=60 sec) after the cooling source has been removed, show that the cold purple tumor begins to warm first at the periphery; it then warms increasingly toward the necrotic center over time. The time series indicates the outer limit or border of the tumor is most accurately identified at time t=0 FIG. 3D. The time series also identifies the existence of two lobes in the melanoma, where the IR image in FIG. 3C taken before cooling indicates a tumor with a single lobe. Thus, DIRI shows the accurate size and shape of the tumor, which in fact comprised a larger area than would be expected if one relied only on the IR image taken before cooling.

Figures 3E, 3F:
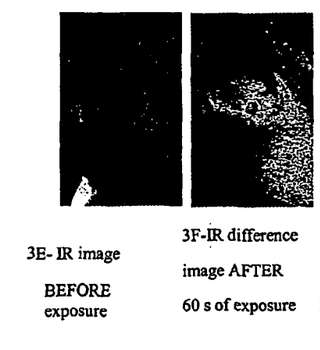
Figure 3G:
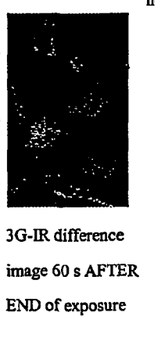

FIGS. 3E-3G are images of the same melanoma tumor before, during and after heating with microwaves. The G361 tumor cells produce excessive amounts of the pigment melanin, that selectively absorbs certain wavelengths of microwave irradiation. This selective absorption facilitates selective heating of the melanin-containing tumor compared with surrounding tissue that typically has less melanin. Melanoma is therefore an example of selective, molecule-specific heating and hence DIRI of a tumor.

Before heating (FIG. 3E), the melanoma is poorly distinguished and appears to be a single sphere or lobe. After 60 seconds of exposure to microwave heating, two areas of high IR emission are clearly visible, indicating that the melanoma is actually composed of two spheres or lobes. This is consistent with the observations after cooling of the melanoma in FIG. 3C and FIG. 3D. The IR image taken 60 seconds after the end of exposure to microwaves revealed two lobes. The results of these DIRI studies show that DIRI gives more information on the physiology (metabolic rate), vascularization and size of tumors than can be obtained with passive IR imaging alone.

Some tumors like colorectal tumors have varying amounts of hypoxic fractions that depend on the genetic background of the tumor type. Tumors of this type are also characterized by high interstitial pressures because the neovascular patterns are abnormal; they have reduced blood flow due to connectivity between the blood vessels entering the tumor and the blood and lymph vessels exiting the tumor. Therefore the difference in recovery after temperature perturbation is not just due to the extent of blood vessels (vascularization), recovery is also affected by the fact that blood does not flow as well through the tumor as normal tissue. In such tumors, diffusion is more important in the tumor than in the surrounding normal tissue, and recovery is therefore slower in more poorly perfused areas of the tumor. The more poorly perfused areas are typically more centrally located in the tumor, and these areas also have more hypoxic and necrotic cells than other areas that are relatively well perfused. In such tumors as these, it is not just the extent of vascularity that renders the tumors different from normal tissues. The decreased functional capacity of the blood vessels to transport blood in the tumor increases the role and importance of diffusion for heat transfer in the tumor. Diffusion is a slower process than blood flow.

Many colorectal tumors are missed in the clinic and thus are not treated. Because colorectal tumors are accessible by endoscopy, DIRI can be used as a new tool for more accurate detection and monitoring of treatment of such tumors.

E. Dynamic IR Imaging (DIRI) of Vascular Tissue

IR images taken as a tissue recovers from heating or cooling, provide distinct information on at least four distinct thermal processes: diffusion from veins, tissue perfusion, blood flow rates in veins, and thermal diffusion from core structures. The thermal response of vascular tissue to cold challenge was studied using active, dynamic IR imaging, according to an illustrated embodiment. The tissue was a human forearm containing a network of arteries, veins and capillaries along with muscle, fat and other tissue. The overall geometry of this network, including its structure and function, is well known and provides a test bed for the new measurement methods of the illustrated embodiment.

In the illustrated embodiment, a room temperature aluminum block of large thermal mass is applied to the forearm to cool the underside of the forearm in a region containing two large veins, several smaller veins and regions where no veins were apparent. Cooling times ranged from a few seconds to twenty seconds. After removal of the aluminum block, an infrared camera in the 3-5 micrometer band captured stacks of images of the cooled region and surrounding uncooled regions over a period of several minutes as the arm recovered to its initial warm-blooded state above ambient temperature. Each pixel in the stack exhibited a distinct time response and each was analyzed to obtain the variation of emitted intensity I(r, t) as a function of pixel position, r, and time, t. For individual pixels in the illustrated embodiment, the intensity response is well described by the function $$I(\underline{r}, t) = A(\underline{r}) - B(\underline{r})\exp(-b(\underline{r})*t) - C(\underline{r})\exp(-c(\underline{r})*t).$$

The values of the parameters (e.g. amplitudes A, B, C and rates b, c) are determined by fitting the function to the time series of images. The parameter values vary spatially, thus describing distinct aspects of the tissue response in different regions.

Figure 4:
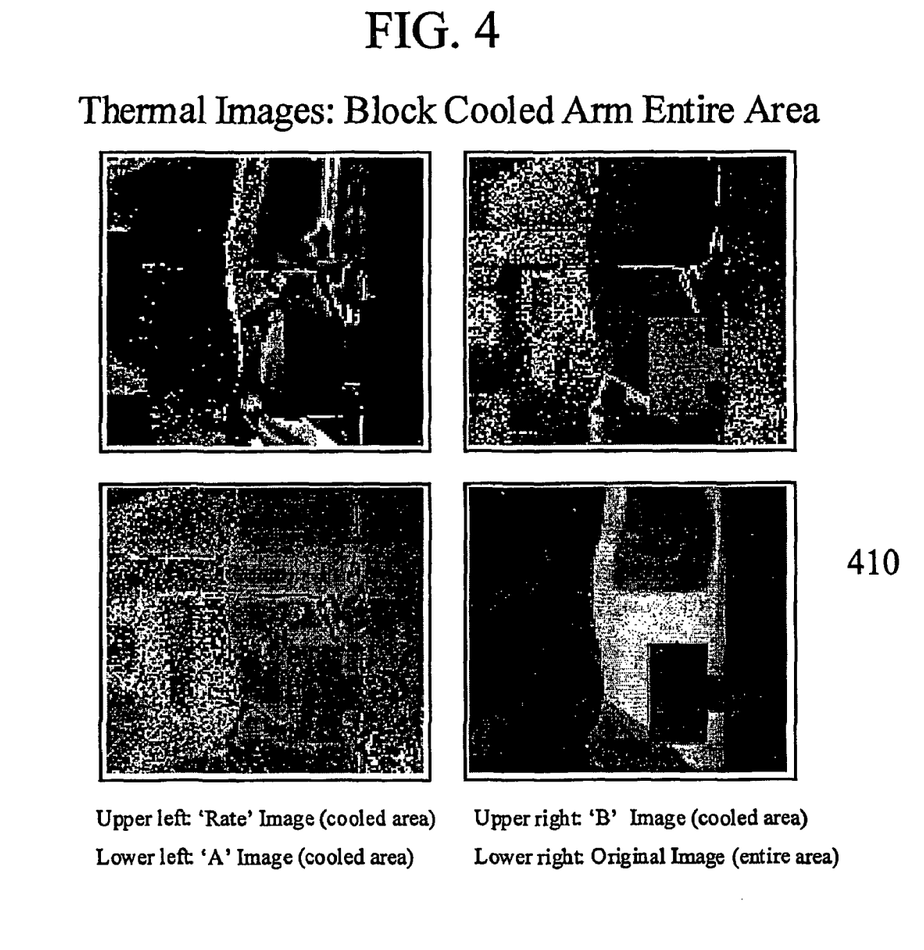
FIG. 4 shows thermal images of block cooling of the entire area of a human arm.

FIG. 4 illustrates the spatial variation of two amplitude parameters, A(r) and B(r), and one rate parameter, b(r), as well as the spatial variation of the IR intensity in the original image, taken at an first time of the time series. For the same view including the forearm and the surrounding area, the upper left image of FIG. 4 shows the spatial variation of the rate parameter, b(r), the lower left image of FIG. 4 shows the spatial variation of the amplitude A(r), the upper right image of FIG. 4 shows the spatial variation of the amplitude B(r), and the lower right image of FIG. 4 shows the original image. The cooled region 410 is evident as the medium gray rectangular region of the forearm intersecting the top of the view in the lower right image.

Figure 5:
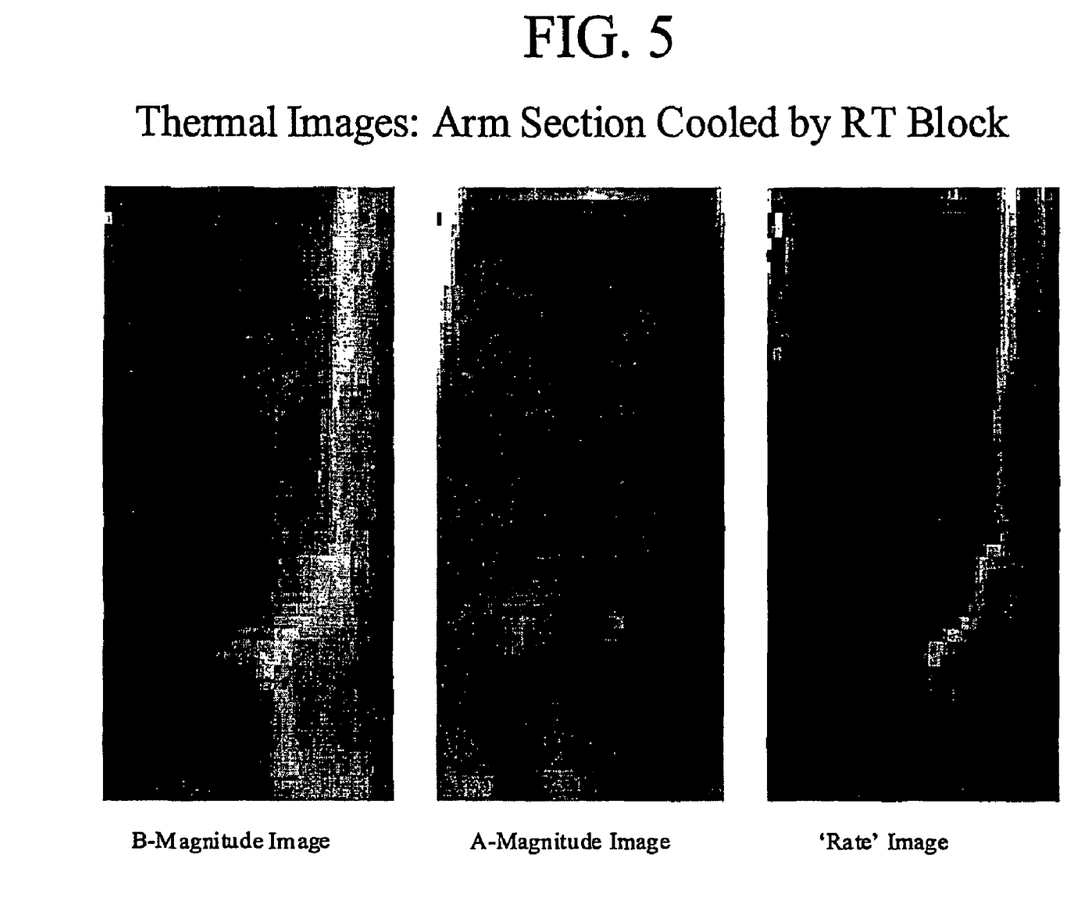
FIG. 5 shows thermal images of a human arm section cooled by RT block.

In a first analysis, illustrated in FIG. 5, DIRI was used to monitor the recovery of the two large veins near the right edge of the cooled area. For the same view including only the right side of the cooled area, the left image of FIG. 5 shows the spatial variation of the amplitude B(r), the middle image of FIG. 5 shows the spatial variation of the amplitude A(r), the right image of FIG. 5 shows the spatial variation of the rate b(r). As explained below, the veins are evident as the bright (large value) pixels in the right image. The recovery is expected to vary as a function of time and location from the point of entry of blood from an uncooled region. At long times, I(r, t)=A(r), so A(r) is relatively uniform spatially along the vein, as illustrated by the middle image of FIG. 5. However, the other parameters show strong spatial variation with a maximum at the point of entry of warm blood into the cooled vein. These parameters are associated with the radial and longitudinal heat transport within the vein and into the surrounding tissue caused by the corresponding parabolic velocity profile for blood flow in veins. Thermal diffusion into the surrounding tissue was confirmed by studying the IR response transverse to the vein extending into the surrounding tissue. In this case the effect of thermal diffusion was seen in both the amplitude and time response parameters e.g. B and b respectively. The variation in profile transverse to the axis of the vein at successive times was used to obtain a value for tissue thermal diffusivity $D_T$=0.0015 cm$^2$s$^{-1}$ which is in general agreement with literature values using conventional models of diffusion from cylindrical objects.

Figure 6:
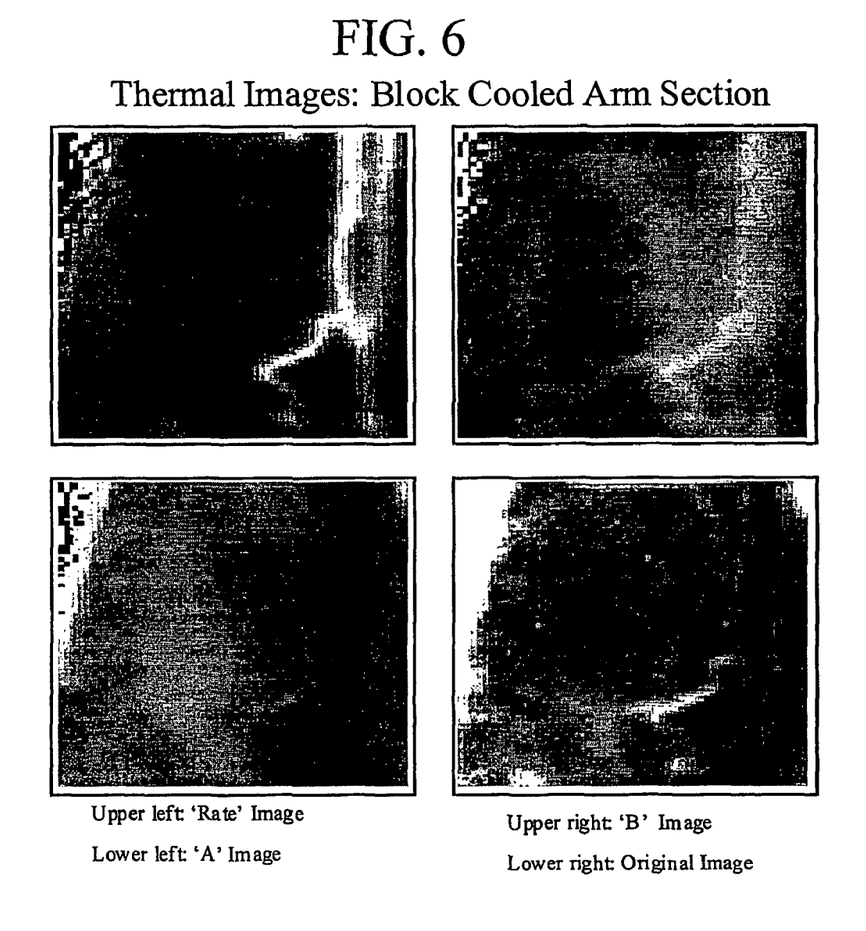
FIG. 6 shows thermal images of a block cooled arm section.

A third analysis, illustrated in FIG. 6, measured the time-temperature response in regions far from any apparent vein. For the same view including only the cooled area, and with the contrast reset to better show variations within the cooled area, the upper left image of FIG. 6 shows the spatial variation of the rate parameter, b(r), the lower left image of FIG. 6 shows the spatial variation of the amplitude A(r), the upper right image of FIG. 6 shows the spatial variation of the amplitude B(r), and the lower right image of FIG. 6 shows the original image. Here the values of b(r) are much smaller on average than those near the vein but show systematic local variation. It is anticipated that these values can be attributed to a combination of thermal diffusion from the interior of the arm and capillary reperfusion linked to vasodilation. It is not yet established if perfusion can be distinguished from diffusion based on the approach of the illustrated embodiment. However, note smaller veins are visible in some images but absent in others. An example is FIG. 6 where the lower right original image shows a branching vein near the top center, which is absent in the upper left rate image. In other cases such 'hidden veins' are present in the b(r) images but absent in the A(r) and other images. Such variations are consistent when it is recognized that the intensity of the b(r) image correlates with the rate of recovery of temperature and hence with the rate of thermal energy release at depth while the A(r) image describes the final intensity distribution. For example, a vein not affected by the cooling source may be expected to appear in the original image and in the image of the amplitude A(r), but not in the rate image or in the image of amplitude B(r), which are sensitive to time varying temperatures.

Advances in sensitivity and precision for detecting and analyzing infrared images, especially after heating or cooling of the target tissue, offer new opportunities to measure temperature gradients in living tissues non-invasively. When coupled to analytical algorithms, precise measurements (temperature change ~20 millikelvin; temporal resolution ~15 milliseconds; and spatial resolution: <100 microns), can be used with embodiments of the invention to characterize the structure of the underlying vasculature or vascular proliferations through unfolding space-time patterns of temperature. The use of perturbation methods, e.g., cold and hot challenge, provides direct information on internal thermal transport and on the presence, location and strength of internal thermal sources in the tissue, tumor or lesion that is not available using visible imaging alone.

What is claimed is:

1. A method for determining the activity of a tumor or lesion using IR imaging, comprising:
   a. imaging the lesion to obtain an IR image of the lesion at a specific orientation at a first time,
   b. imaging the lesion to obtain an optical image of the lesion at a second time that is close to the first time at substantially the same specific orientation,
   c. comparing the IR image and the optical image to determine the relative size and perimeter of the lesion, and
   d. determining that the lesion is active if at least one of the size and the perimeter of the lesion in the IR image is significantly larger than the size and the perimeter of the lesion in the optical image, respectively.

2. The method of claim 1, wherein the lesion is a member of the group comprising a Kaposi's sarcoma lesion, a basal cell carcinoma and a melanoma.

3. A method for determining a characteristic of a tumor or lesion, comprising:
   a. obtaining a first infrared image of the tumor or lesion and the surrounding tissue at a first time at ambient temperature,
   b. identifying a first pattern of infrared emission in the first infrared image,
   c. heating or cooling the tumor or lesion and the area of tissue surrounding the tumor or lesion to a desired temperature,
   d. obtaining a second infrared image of the tumor or lesion and the surrounding tissue at the desired temperature,
   e. identifying a second pattern of infrared emission in the second infrared image,
   f. comparing the first and second patterns of infrared emission to determine differences in infrared intensity between the first and second patterns of infrared emission, and
   g. characterizing the tumor or lesion based on the differences in infrared intensity between the first and second patterns of infrared emission.

4. The method of claim 3, wherein step c is heating the tumor or lesion and the differences in infrared intensity between the first and second patterns of infrared emission in step f characterize the tumor or lesion based on vascularization.

5. The method of claim 3, wherein step c is heating the tumor or lesion and the differences in infrared intensity between the first and second patterns of infrared emission in step f characterize the tumor or lesion based on metabolic activity.

6. A method for determining a characteristic of a tumor or lesion, comprising:
   a. heating or cooling the tumor or lesion and an area of tissue surrounding the tumor or lesion to a desired temperature,
   b. removing the heating or cooling source,
   c. obtaining a first infrared image of the tumor or lesion and the surrounding tissue at a first time after removing the heating or cooling source,
   d. identifying a first pattern of infrared emission in the first infrared image,
   e. repeating step c at a second time after removing the heating or cooling source to obtain a second infrared image,
   f. identifying a second pattern of infrared emission in the second infrared image,
   g. comparing the first and second patterns of infrared emission to determine differences in infrared intensity between the first and second patterns of infrared emission, and
   h. characterizing the tumor or lesion based on the differences in infrared intensity between the first and second patterns of infrared emission.

7. The method of claim 6, wherein step a is heating the tumor or lesion, and wherein the differences in infrared intensity between the first and second patterns of infrared emission in step h characterize the tumor or lesion based on vascularization.

8. The method of claim 6, wherein step a is heating the tumor or lesion, and wherein the differences in infrared intensity between the first and second patterns of infrared emission in step h characterize the tumor or lesion based on metabolic activity.

9. A method for determining the efficacy of treatment of a cancerous mass using dynamic infrared imaging, comprising:
   a. heating or cooling the mass to a desired first temperature at a first stage before or during therapy,
   b. removing the heating or cooling source,
   c. obtaining a first infrared image of the mass at a first time after removing the heating or cooling source,
   d. obtaining a second infrared image of the mass,
   e. comparing the first and second infrared images to identify areas of different infrared emission associated with the mass,
   f. heating or cooling the mass to the desired first temperature at a second stage after further therapy,
   g. repeating steps b-e,
   h. comparing the areas of different infrared emission at the first stage with the areas of different infrared emission at the second stage, and
   i. determining that therapy is effective if the areas with different infrared emission at the second stage are smaller than the areas of different infrared emission at the first stage.

10. The method of claim 9, wherein areas of different infrared emission correspond to areas of higher than average metabolic activity.

11. The method of claim 9, wherein areas of different infrared emission correspond to areas of lower than average metabolic activity.

12. The method of claim 9, wherein areas of different infrared emission correspond to areas of higher than average vascularization.

13. The method of claim 9, wherein areas of different infrared emission correspond to areas of lower than average vascularization.

14. The method of claim 9, wherein the therapy is drug therapy.

15. The method of claim 14, wherein the drug is an anti-angiogenesis factor.

16. The method of claim 9, wherein the therapy is radiation therapy.

17. The method of claim 16, wherein the radiation is x-ray radiation.

18. The method of claim 16, wherein the radiation is thermal radiation.

19. The method of claim 16, wherein the radiation is ultrasonic radiation.

20. The method of claim 16, wherein the radiation is microwave radiation.

21. A method for determining the activity of a Kaposi's sarcoma lesion having an observable pigmented area using IR imaging, comprising:
   a. imaging the Kaposi's sarcoma lesion to obtaining an IR image,
   b. examining the IR image to determine if a size and a perimeter of the pigmented area can be identified in the IR image,
   c. determining if the size and perimeter of the pigmented area can be identified,
   d. comparing the size and perimeter of the pigmented area to the size and perimeter of a thermal image of the area in the IR image, and
   e. determining that the area is active if the size and perimeter of the thermal image is significantly larger than the size and perimeter of the pigmented area, respectively.

22. The method as in one of claims 21, 3, 6 and 9, wherein the infrared image is of infrared light that has a wavelength from about 2 microns to about 30 microns.

* * * * *